(12) United States Patent  
Segall

(10) Patent No.: US 9,134,232 B1
(45) Date of Patent: Sep. 15, 2015

(54) LASER INSPECTION SYSTEM

(71) Applicant: Stephen Barrett Segall, Ann Arbor, MI (US)

(72) Inventor: Stephen Barrett Segall, Ann Arbor, MI (US)

(73) Assignee: Industrial Optical Measurement Systems, LLC, Ann Arbor, MI (US)

( * ) Notice: Subject to any disclaimer, the term of this patent is extended or adjusted under 35 U.S.C. 154(b) by 77 days.

(21) Appl. No.: 14/081,650

(22) Filed: Nov. 15, 2013

Related U.S. Application Data

(60) Provisional application No. 61/726,826, filed on Nov. 15, 2012.

(51) Int. Cl.
  *G01B 11/24* (2006.01)
  *G01N 21/55* (2014.01)
  *G01N 21/21* (2006.01)

(52) U.S. Cl.
  CPC ............... *G01N 21/55* (2013.01); *G01N 21/21* (2013.01)

(58) Field of Classification Search
  CPC ......... G01B 11/24; G01N 21/55; G01N 21/21
  USPC .................................................. 356/602, 608
  See application file for complete search history.

(56) References Cited

U.S. PATENT DOCUMENTS

| | | |
|---|---|---|
| 3,761,186 A * | 9/1973 | Wason .................. 356/241.1 |
| 4,055,382 A | 10/1977 | Ziekman et al. |
| 4,315,688 A | 2/1982 | Pryor |
| 4,440,496 A | 4/1984 | Milana |
| 4,461,569 A | 7/1984 | Corbett |
| 4,505,585 A | 3/1985 | Yoshikawa et al. |
| 4,508,450 A | 4/1985 | Ohshima et al. |
| 4,555,727 A | 11/1985 | Nun et al. |
| H230 H * | 3/1987 | Smith .......................... 356/369 |
| 4,669,885 A | 6/1987 | Ina |
| 4,732,474 A | 3/1988 | Chikama |
| 5,033,856 A | 7/1991 | Nose et al. |
| 5,054,087 A | 10/1991 | Carbon et al. |
| 5,315,374 A | 5/1994 | Yoshizumi |
| 5,317,387 A * | 5/1994 | Van Hengel et al. ......... 356/625 |
| 5,353,357 A | 10/1994 | Longest, Jr. et al. |
| 5,424,834 A | 6/1995 | Akedo et al. |
| 5,585,917 A | 12/1996 | Woite et al. |
| 5,588,068 A | 12/1996 | Longest et al. |
| 5,636,024 A | 6/1997 | Crookham et al. |
| 5,646,724 A | 7/1997 | Hershline |
| 5,936,725 A | 8/1999 | Pike et al. |
| 6,097,482 A | 8/2000 | Smith et al. |
| 6,169,600 B1 | 1/2001 | Ludlow |
| 6,516,083 B1 | 2/2003 | Bonechi et al. |
| 6,603,540 B1 | 8/2003 | Kaupp |
| 6,661,508 B2 | 12/2003 | Eytan et al. |

(Continued)

*Primary Examiner* — Roy M Punnoose
(74) *Attorney, Agent, or Firm* — Vivacqua Law, PLLC; Raymond J. Vivacqua; John M. Card

(57) ABSTRACT

A non-contact optical probe for inspecting an inside surface of a cylindrical workpiece includes a laser source that emits an incident light beam, a polarizing beam splitter that transmits one polarization of the incident beam and reflects the opposite polarization, a quarter wave plate that together with the polarizing beam splitter separates back reflected return light from the incident laser beam, a probe tip that directs the incident laser beam onto the cylinder surface and directs reflected light from the surface back to the beam splitter, and at least one detector that receives a portion of the reflected light and generates data about the cylinder surface.

9 Claims, 16 Drawing Sheets

(56) References Cited

U.S. PATENT DOCUMENTS

| | | |
|---|---|---|
| 7,027,145 B2 | 4/2006 | Segall et al. |
| 7,327,447 B2 | 2/2008 | Ovadia |
| 7,342,654 B2 | 3/2008 | Laue et al. |
| 7,372,557 B2 | 5/2008 | Oomori et al. |
| 7,394,530 B2 | 7/2008 | Budd |
| 2001/0015804 A1 | 8/2001 | Doyle, Jr. |
| 2004/0201856 A1* | 10/2004 | Quadling et al. ............. 356/601 |
| 2011/0080588 A1 | 4/2011 | Segall |

* cited by examiner

LASER INSPECTION SYSTEM

RELATED APPLICATION

This application claims the benefit of U.S. Provisional Patent Application No. 61/726,826, filed on Nov. 15, 2012, the entire contents of which is incorporated herein by reference.

FEDERALLY SPONSORED RESEARCH

Certain of the research leading to the present invention was sponsored by the United States Government under National Science Foundation Grant IIP-0739472. The United States Government has certain rights to the invention.

FIELD

The present disclosure relates to non-contact laser inspection systems and more particularly to non-contact laser inspection systems for detection of surface defects on reflective or partially reflective cylindrical or cylindrically symmetric parts.

BACKGROUND

High volume automated manufacturing systems are very good at producing large number of identical interchangeable parts. However, unless there is adequate inspection of the output of these systems, if they drift out of compliance and start producing parts that are out of tolerance or start producing defective components due to chipped tools or other causes, they can produce very large quantities of identical defective parts before the problem is detected. The material from which a part is produced can also contain defects, such as pores or scratches that would cause a finished part to be rejected as defective.

If defective components enter the assembly stream for a manufactured product, such as a vehicle or appliance, the cost of detecting and correcting a defect can increase exponentially. This cost includes the cost of detecting the problem, disassembling the product to identify the component causing the problem, and identifying and correcting the source of the component defect. It may involve shutting down a production line until the source of the problem is identified and corrected. If finished products are shipped with defective components, the cost of fixing the problem could also involve product returns and warranty repairs.

There is, therefore, a high priority placed on identifying defective components at the earliest possible stage of production to minimize scrap and prevent defective components from entering the assembly stream. In a high volume automated production system inspection of parts by human inspectors is subjective and inadequate. It is preferable to have inspection techniques that can be automated to detect defects at the rate of production according to objective criteria. Non contact inspection methods are preferred because they do not involve the use of mechanical gauges that can wear and need to be periodically replaced. Optical inspection of components is one of these non contact inspection techniques. It is often preferred for detecting surface defects in manufactured components because it can rapidly collect and analyze high resolution data.

A number of non contact optical devices have been developed over the past several years for the inspection of manufactured surfaces in a production environment. These can be divided into two broad categories according to the light source that is used—laser scanning devices and machine vision systems employing broadband unpolarized or white light sources. Each of these two approaches to optical inspection can be divided into two main classes of devices—those that inspect the exterior surfaces of components and those that inspect the interior surfaces. Devices that inspect exterior surfaces that are flat or have a curved profile may not be capable of inspecting the interior surfaces of cylindrical objects. Some vision systems developed for external inspection can see inside containers, but their inspection capabilities are limited, especially if a container is long and narrow, such as the case of some cylinders.

Accordingly, there is a need in the art for an improved non-contact laser inspection system capable of rapidly detecting surface defects and surface profile variations using laser light to inspect cylinder bores.

SUMMARY

A non-contact optical probe for inspecting an inside surface of a cylindrical workpiece includes a laser source that emits an incident light beam, a polarizing beam splitter that transmits one polarization of the incident beam and reflects the opposite polarization, a quarter wave plate that together with the polarizing beam splitter separates back reflected return light from the transmitted incident laser beam, a probe tip that directs the transmitted incident laser beam onto the cylinder surface and directs reflected light from the surface back to the beam splitter, and at least one detector that receives a portion of the reflected light and generates data about the cylinder surface.

In another aspect, a non-contact optical probe for inspecting a cylindrical surface of a workpiece includes a laser source that emits an incident light beam, a first reflector that directs the incident light beam onto the cylindrical surface, a reflector that receives scattered light from the cylindrical surface, and an optical system that images the spot of scattered light on the cylindrical surface onto the surface of a detector. The detector receives the scattered light from the imaging system and generates signals that provide imaging data as well as displacement information through triangulation. One of the techniques used to transmit data from the optical probe to a data acquisition system may be applicable to a wider class of rotating equipment.

In yet another aspect, a non-contact probe for inspecting a cylindrical surface of a workpiece includes a laser source that emits an incident light beam, a polarizing beam splitter that transmits one direction of polarization of the incident laser beam and reflects the other direction of polarization, a quarter wave plate that converts the transmitted incident beam from linear polarization to circular polarization, a first reflector that directs the incident light beam onto a cylinder surface and receives reflected light from the cylindrical surface, a second reflector that receives scattered light from the cylindrical surface, a first detector that receives the return reflected light from the polarizing beam splitter, and a second detector that receives scattered light from the cylinder surface that is deflected by the second reflector. The first detector and the second detector generate signals related to reflected and scattered scanning data from the surface.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses. It is to be understood that standard components or features that are within the purview of an artisan of ordinary skill and do not contribute to the understanding of the various embodiments of the invention may be omitted from the drawings to enhance clarity. In addition it will be appreciated that the characterization of various components and orientations described herein as being "vertical" or "horizontal", "right" or "left", "side", "top" or "bottom" are relative characterizations only based upon the particular position or orientation of a given component for a particular application.

Figure 1:
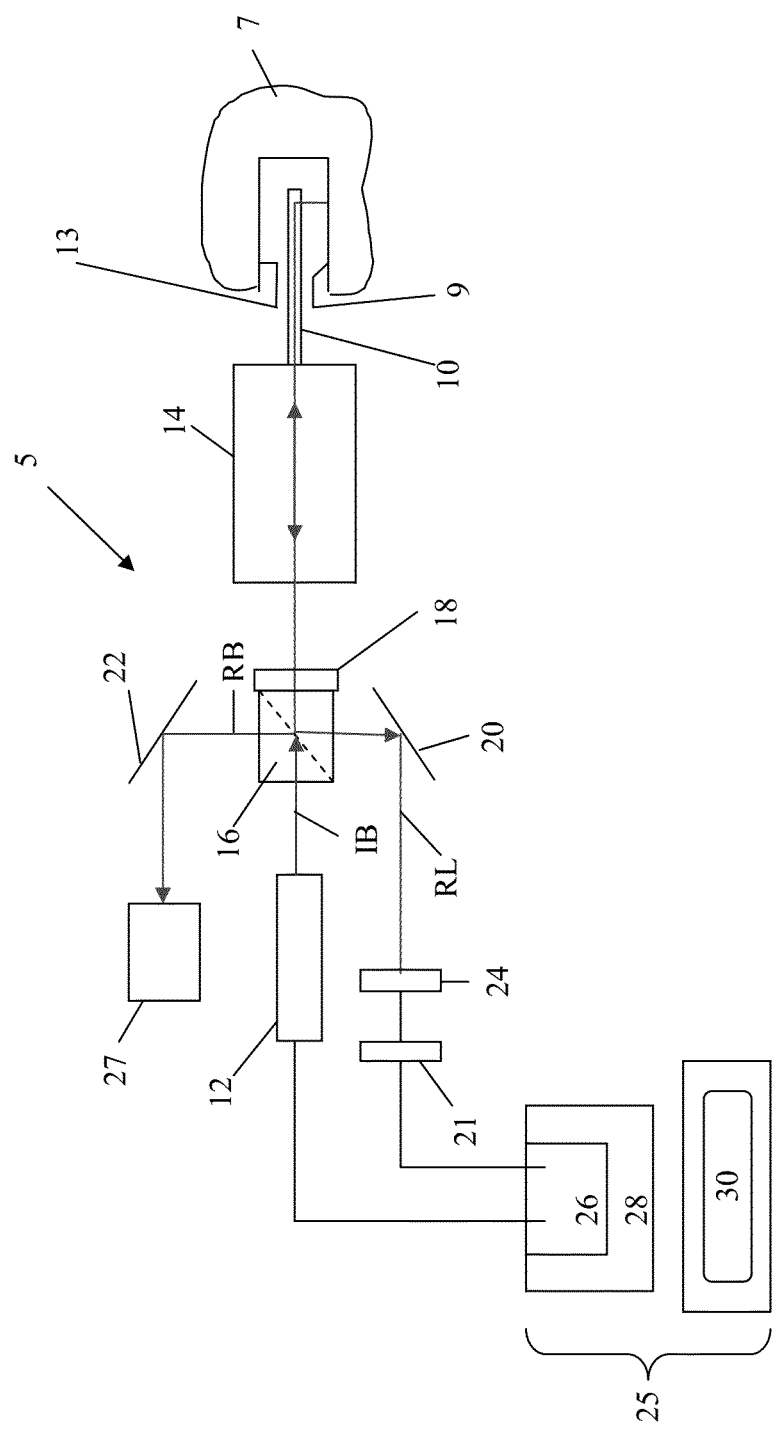
FIG. 1 is schematic drawing of an inspection probe system detecting back reflected light in accordance with the principles of the present invention.

With reference to FIG. 1, a schematic diagram of inspection probe system 5 for inspecting workpiece 7 is shown. Inspection probe system 5 includes a probe tip 10, a laser 12, a spindle 14, a polarizing beam splitter 16, a quarter wave plate 18, a pair of mirrors 20 and 22, a detector 24, electronics for processing the detector signal 21, a beam dump 27, and a control and processing unit 25, including a data acquisition unit 26, a computer 28, and a monitor 30. FIG. 1 does not include motion stages that would be needed for the operation of a complete inspection station.

Workpiece 7 includes an at least partially reflective inner surface 9 that defines at least one bore 13. In the example provided, bore 13 is a valve port and workpiece 7 is a valve body or pump cover in a transmission of an automobile. However, it should be appreciated that cylindrical bore 13 could exist in many other types of workpieces 7, such as, but not limited to, brake cylinders, shock absorbers, hydraulic or pneumatic cylinders, gas flow valves, tapped internally threaded cylinders or other cylindrical manufactured parts. The description of the invention is merely exemplary in nature and variations that do not depart from the gist of the invention are intended to be within the scope of the invention. Such variations are not to be regarded as a departure from the spirit and scope of the invention.

Probe tip 10 is disposed in the bore 13. Probe tip 10 is generally part of a laser inspection system 5 receiving emitted light IB from laser 12. Probe tip 10 is attached to and centered on spindle 14.

Data acquisition unit 26 may be an internal data acquisition card installed in computer 28 or an external data collection unit in communication with computer 28. Data acquisition unit 26 may also be able to provide power to laser 12. Alternatively, a separate regulated power supply could provide power to laser 12. Other types of devices, however, that perform the same functions as computer 28 may be employed without departing from the scope of the present invention. Data acquisition unit 26 may be in communication with a rotary encoder and a linear encoder and receives signals from signal processing electronics 21 of detector 24.

Polarizing beam splitter 16 is positioned between laser 12 and spindle 14. Polarizing beam splitter 16 transmits one component of polarization of incident laser beam IB and reflects the perpendicular polarization RB. When laser 12 generates a linearly polarized beam of light, the laser can be oriented so that the polarization of beam IB from laser 12 substantially passes through polarizing beam splitter 16. Quarter wave plate 18 converts incident laser beam IB from laser 12 that is transmitted through polarizing beam splitter 16 from linear to circular polarization. Quarter wave plate 18 also converts the return reflected light RL from cylinder surface 9 from circular back to linear polarization, but with a direction of polarization perpendicular to the incident direction of polarization, which causes the portion of return light RL with linear polarization perpendicular to the incident direction of polarization to be reflected toward mirror 20 and detector 24. A non-polarizing beam splitter could be employed without a quarter wave plate, but much of the incident beam IB and reflected light RL would be lost.

When a fiber laser is used to generate a small laser spot on cylinder surface 9, the laser output beam IB will not be linearly polarized. Half the laser output will be reflected by polarizing prism 16 into rejected beam RB and not be transmitted to cylinder surface 9. To prevent this light from scattering inside the probe apparatus and affecting the operation of probe inspection system 5, rejected beam RB could be directed to beam dump 27, where it is absorbed. Beam dump 27 could also be used to absorb unwanted reflected light if a linearly polarized laser beam IB is not precisely aligned for maximum transmission through polarizing prism 16.

Mirror 22 reflects that part of the laser output beam RB rejected by polarizing beam splitter 16 to beam dump 27, and mirror 20 reflects the return beam from cylinder surface 9 reflected by polarizing beam splitter 16 to detector 24.

Probe system 5 produces an image of surface 9 of cylinder 13 by scanning surface 9. A linear motion stage is used to move spindle 14 relative to part 7 to scan surface 9 of cylinder 13 as tip 10 rotates. Probe 5 collects directly back reflected and backscattered light RL and generates an image of collected light intensity of surface 9 that can be used to identify surface defects. Probe system 5, however, does not measure displacement.

In probe system 5, the polarization of the component of incident beam IB transmitted through polarizing beam splitter 16 is orthogonal to the polarization of the component of incident beam RB that is rejected. Beams with orthogonal polarizations cannot interfere. But because quarter wave plate 18 rotates the polarization of return light RL relative to incident beam IB by 90°, the rejected component RB of incident beam IB and return light RL reflected by polarizing beam splitter 16 will have the same polarization and can be made to interfere. This is the case in inspection system 105 shown in FIG. 2. By utilizing rejected component RB of incident laser beam IB as a reference beam, an interference pattern can be generated and employed to obtain additional profile information about surface 9.

Figure 2:
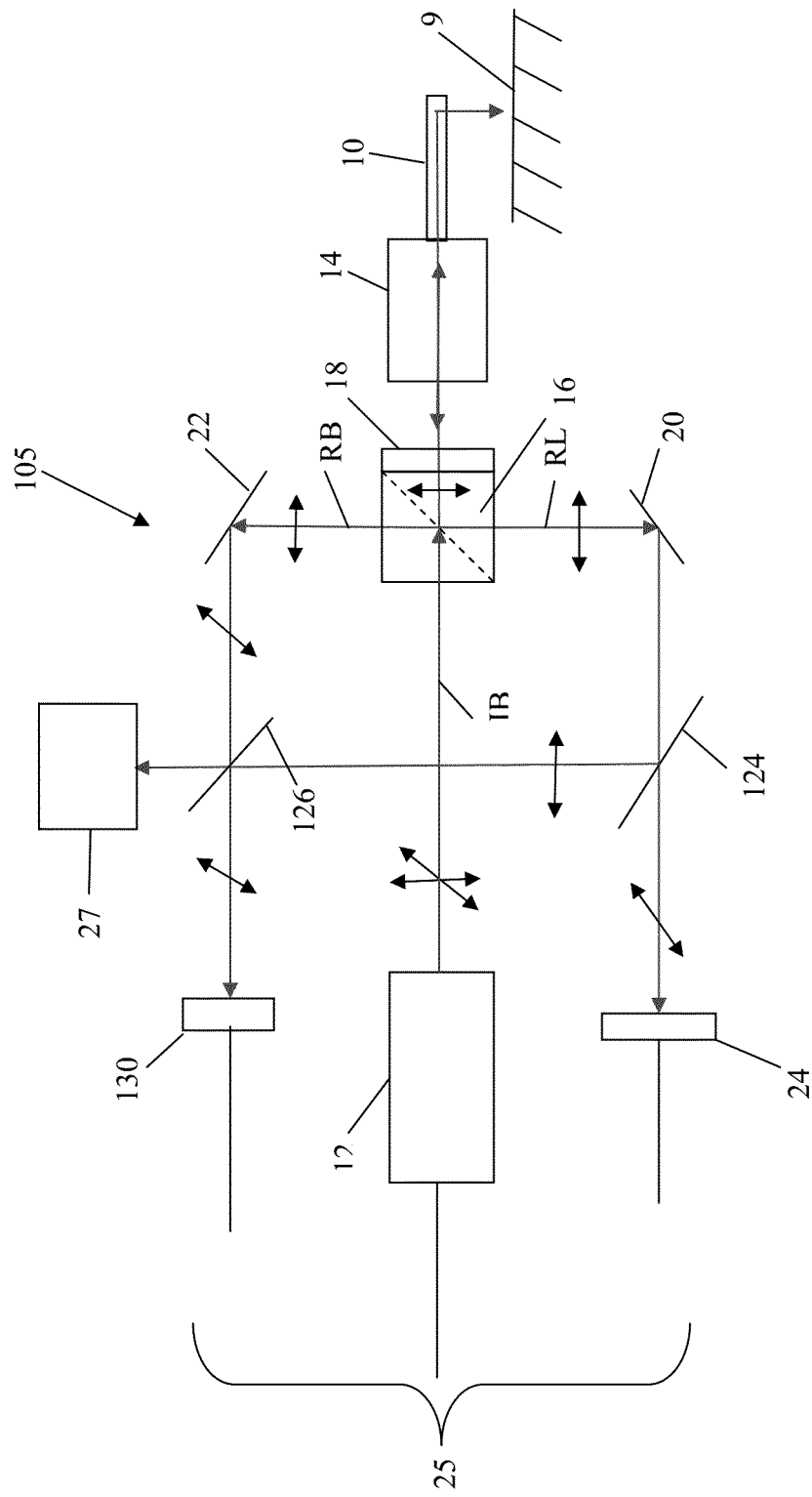
FIG. 2 is a schematic drawing of another inspection probe system detecting back reflected light in accordance with the principles of the present invention.

The inspection system of FIG. 2 makes use of some of the light that was disposed of in beam dump 27 in FIG. 1 to obtain displacement information about cylinder 13 using interferometry. In addition to the components described earlier, the inspection system includes a pair of partially transmitting mirrors 124 and 126 and a second detector 130. Accordingly, rejected beam RB from mirror 22 is directed to partially transmitting mirror 126 from which a small portion (for example, a few percent) of the beam energy is directed to second detector 130, which is substantially similar to first detector 24. The rest of the beam energy that is not transmitted to second detector 130 is reflected to beam dump 27. Electronic processing circuits are employed for detectors 24 and 130.

A flat glass plate with one side uncoated or coated with a partially reflecting coating and the other side with an anti reflection coating could perform the task of partially reflecting mirror 126. Partially reflecting mirror 124 that receives the return light RL from mirror 20 can be a flat glass plate that is anti reflection coated on one side. As such, partially reflecting mirror 124 reflects a small portion (for example, a few percent) of the return light RL to the partially transmitting mirror 126, where most of the reflected light will be reflected into the second detector 130. Hence, part of return light RL and part of rejected incident beam RB will interfere. Thus, inspection system 105 generates a fringe pattern detected with detector 130 as the laser probe scans surface 9 of cylinder 13 in addition to an image of surface 9 produced with detector 24. Specifically, as incident beam IB scans cylinder surface 9 an image of the interference pattern is generated by the inspection system 105 from light collected by detector 130 and transmitted to data acquisition system 26. The interference pattern is superimposed on the image of surface 9. The image of surface 9 obtained from detector 24 can be subtracted from the image containing the fringes obtained from detector 130 to produce only the interference pattern.

There is less laser energy in the laser light directed to the second detector 130. This does not affect the quality of the image, because neutral density filters are usually employed in detector 24 to prevent return light RL from saturating detector 24. A neutral density filter could be placed in front of detector 24. The second detector 130 can have fewer or no neutral density filters.

The interference pattern obtained using detector 130 can be used to determine how well probe tip 10 is aligned relative to surface 9 of part 13. It can also be used to determine a surface profile, which is a three dimensional effect that is different than the two dimensional image of surface 9. Since misalignment and surface profile have different characteristic patterns, misalignment can be subtracted from the profile generated from the data collected by detector 130 to produce only the surface profile.

Figure 3:
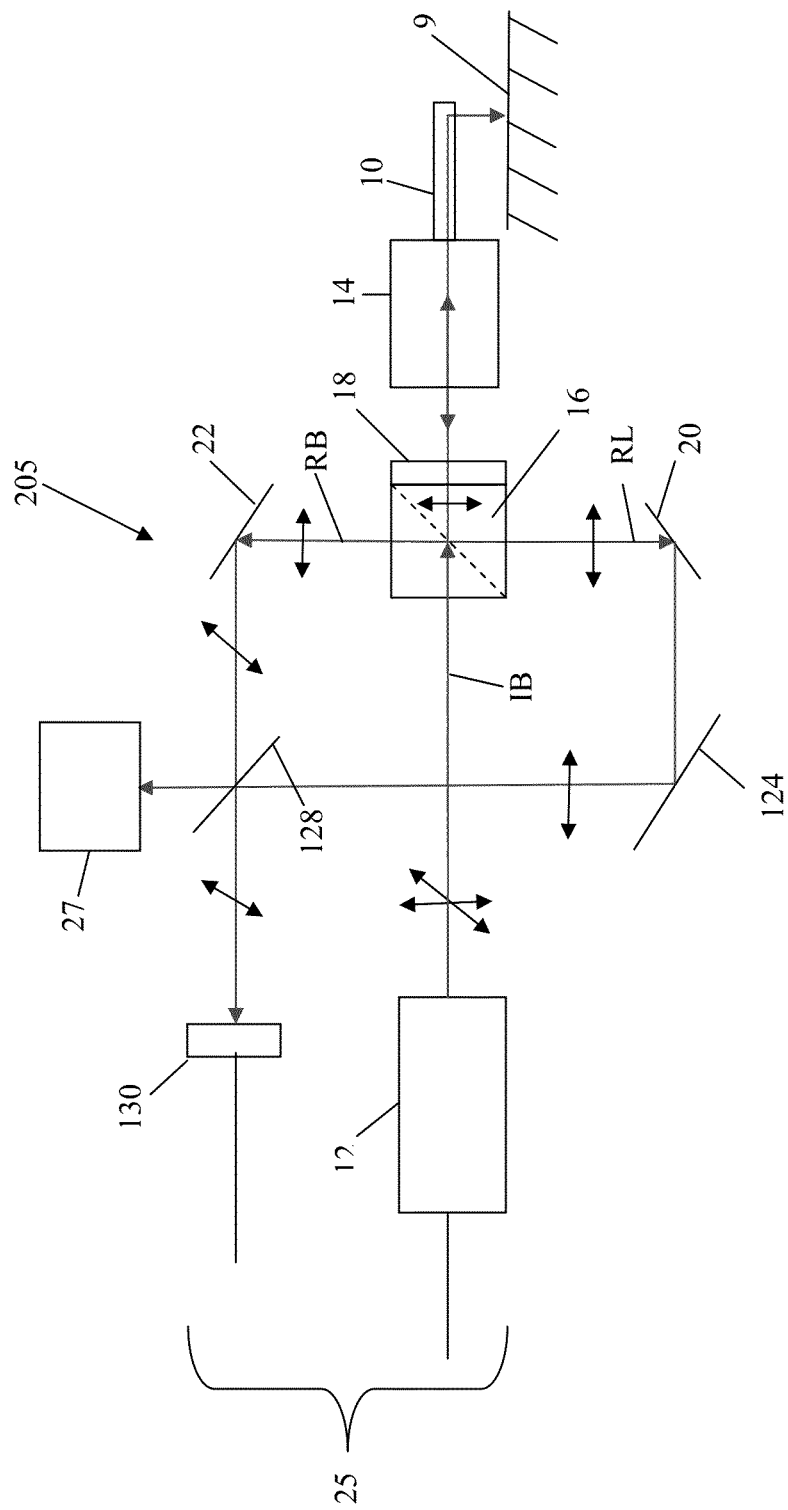
FIG. 3 is a schematic drawing of yet another inspection probe system detecting back reflected light in accordance with the principles of the present invention.

If only the image with superimposed fringes is desired, only one detector (detector 130) could be employed with rejected beam RB interfering with return light RL, as shown in system 205 of FIG. 3. Beam dump 27 may be needed to dispose of excess light transmitted by partially transmitting mirror 124. The beam dump could be a neutral density filter.

A similar interference technique can be used without a fiber laser by rotating a laser with a linearly polarized incident beam IB so that part of the incident beam is rejected by polarizing prism 16. This rejected component RB can be used as a reference beam. In this arrangement less of the beam energy needs to be transmitted to beam dump 27 because the fraction of the laser energy that is rejected can be controlled by rotating the incident plane of polarization, and partially transmitting mirror 126 can transmit a larger fraction of rejected beam RB.

Figure 4:
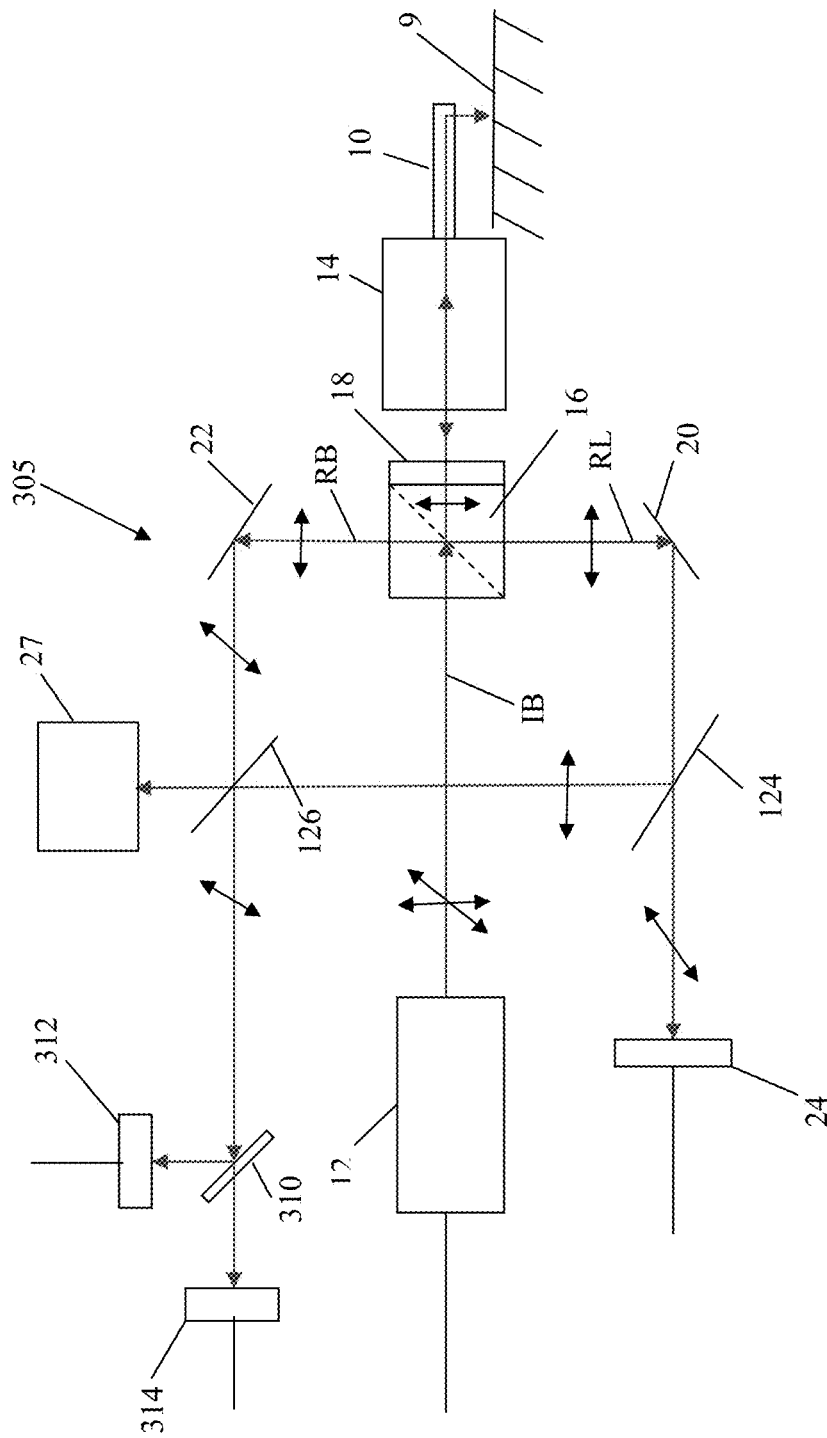
FIG. 4 is a schematic drawing of yet another inspection probe system detecting back reflected light in accordance with the principles of the present invention.

In another arrangement, shown in system 305 of FIG. 4, two laser wavelengths are input simultaneously into a fiber laser 12 and a dichroic mirror 310 is used to separate the signals from the different wavelengths when measuring fringes. Two detectors 312, 314, instead of one detector 130, collect the different wavelengths of light that can be used to produce fringe patterns at the two different wavelengths. The additional information provided indicates whether surface 9 is moving closer to or farther from probe tip 10 as the probe system proceeds into cylinder 13.

To obtain a surface profile from a fringe pattern, the number of fringes is counted as a function of distance along the cylinder and the change in the fringes indicates the surface is moving closer to the probe tip 10 or farther from the probe tip 10. Counting fringes at two different wavelengths enables determining the phase shift between the fringe patterns. This can be accomplished by analyzing the fringe pattern produced as a function of position in the fringe data file for each laser wavelength.

In another embodiment of this device for performing reflective measurements in cylinders, the laser, optics and electronics all spin together and a slip ring or device with a similar function is employed to supply power and collect data from the rotating probe. Such systems are described in U.S. patent application Ser. No. 12/879,245, entitled "NON-CON- TACT LASER INSPECTION SYSTEM" and filed Sep. 10, 2010, the entire contents of which are incorporated herein by reference.

When a slip ring or equivalent device is employed, the probe is able to detect either scattered light or back reflected light, depending on how it is configured. A configuration that detects scatted light is described in U.S. Pat. No. 7,027,145, the entire contents of which are incorporated herein by reference. Laser inspection probes that detect scattered light may be used to inspect cylinders with a pattern of machining marks on their surface, such as bored or honed surfaces of combustion cylinders. These cylinders have diameters on the order of tens of millimeters or greater, so that small diameter tips are not required to scan the cylinder surface.

Probes in which the laser, electronics and optics spin as a unit are mounted on a shaft that is attached to a spindle and the input power cables and output data cables go through a hole in the shaft and spindle rotor to a slip ring in back of the spindle. A pentaprism can be used as a 90° reflector instead of a mirror to deflect light to cylinder surface 9. The laser module used in the probe may incorporate its own focusing optics or an optional beam reducer or focusing optics may be used to reduce the size of the laser spot on cylinder surface 9 being inspected. For a scattered light measurement a mirror deflects light from the cylinder surface onto the detector. The mirror can be moved closer or farther from the detector to collect scattered light at the same mean angle for different diameter cylinders. An envelope is used to cover and protect the section of the probe containing the laser, optics and detector. The envelope has holes or slots to permit laser light to reach the cylinder surface and to permit scattered light to hit the deflecting mirror. Compressed clean air at a low pressure can be injected through the probe shaft and flow through the probe body to establish a positive pressure inside the probe to keep outside air from reaching exposed optical components.

Often combustion cylinders are plateau honed to smooth sharp peaks generated by the previous honing process. This can reduce friction between piston rings and the cylinder wall when an internal combustion engine is operating, while still permitting honing grooves to retain lubricant as the piston moves up and down inside the cylinder. The amount of plateau honing is a parameter that manufacturers wish to optimize. A probe that measures reflectivity could be used to measure the coefficient of reflectivity of these plateau honed cylinders and relate this to the amount of plateau honing in the cylinder.

While a probe that detects back reflected light can also detect machining marks, a probe that detects scattered light can provide better resolution of the machining mark patterns that help to more easily identify defective honing patterns.

Figure 5:
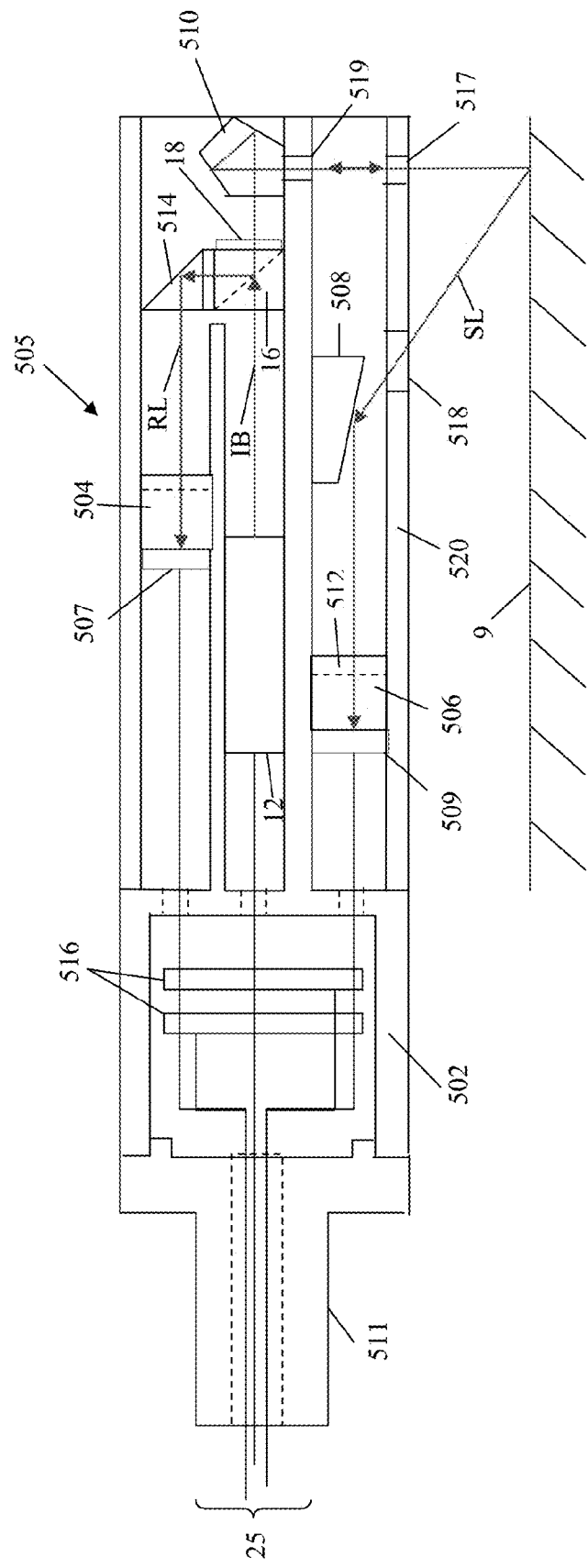
FIG. 5 is a schematic drawing of yet another inspection probe for detecting both back reflected and scattered light in accordance with the principles of the present invention.

A hybrid version of a probe, such as probe 505 shown in FIG. 5 in which the entire probe spins, measures both scattered and reflected light from a cylinder surface simultaneously. In probe 505 laser module 12 emits incident beam IB with a linear polarization that is transmitted through polarizing prism 16. The polarization is converted from linear to circular polarization by quarter wave plate 18 and IB is transmitted to pentaprism 510. Pentaprism 510 deflects IB by 90° and through aperture 519 and aperture 517 in probe envelope 520 to cylindrical surface 9. Scattered light SL from surface 9 is transmitted though aperture 518 in probe envelope 520 and deflected by mirror 508 into detector holder 506 which holds detector 509 and its wavelength bandpass filter 512 in place.

The signal from detector 509 is processed by electronic circuit 516 mounted in probe body housing 502. The electronic signal, proportional to detected laser intensity, is transmitted though probe mounting shaft 511, through the spindle on which the shaft is mounted, and through the slip ring to data collection, analysis and display system 25.

Part of the light from the laser spot on surface 9 is back reflected through apertures 517, 519 and pentaprism 510 and through quarter wave plate 18 where it is converted from circularly polarized to linearly polarized light 90° out of phase with incident beam IB. Therefore, reflected light RL is reflected by polarizing prism 16 and right angle prism 514 through detector and wavelength filter holder 504 to detector 507. The signal from detector 507 is processed by electronic circuit 516 and sent through shaft 511 to data processing system 25. This enables probe 505 to collect both scattered and reflected light from the cylinder surface simultaneously. Electronic circuits 516 could be mounted on a single circuit board or on a single integrated circuit.

An advantage of using pentaprism 510 in probe 505 to reflect incident laser beam IB is that even if pentaprism 510 is slightly misaligned, light from the laser will be reflected at a 90° angle relative to the direction of incident beam IB when it exits laser 12. The transmitting faces of pentaprism 510 are anti-reflection coated to minimize the amount of emitted light reflected from the air-glass interfaces of pentaprism 510 back to the reflected light detector 507, since this detector detects the sum of the signals from the cylinder surface and the air-glass interfaces of pentaprism 510. A rod mirror may be used in place of pentaprism 510 to eliminate issues of back reflected light from the pentaprism air-glass interface.

Figure 6:
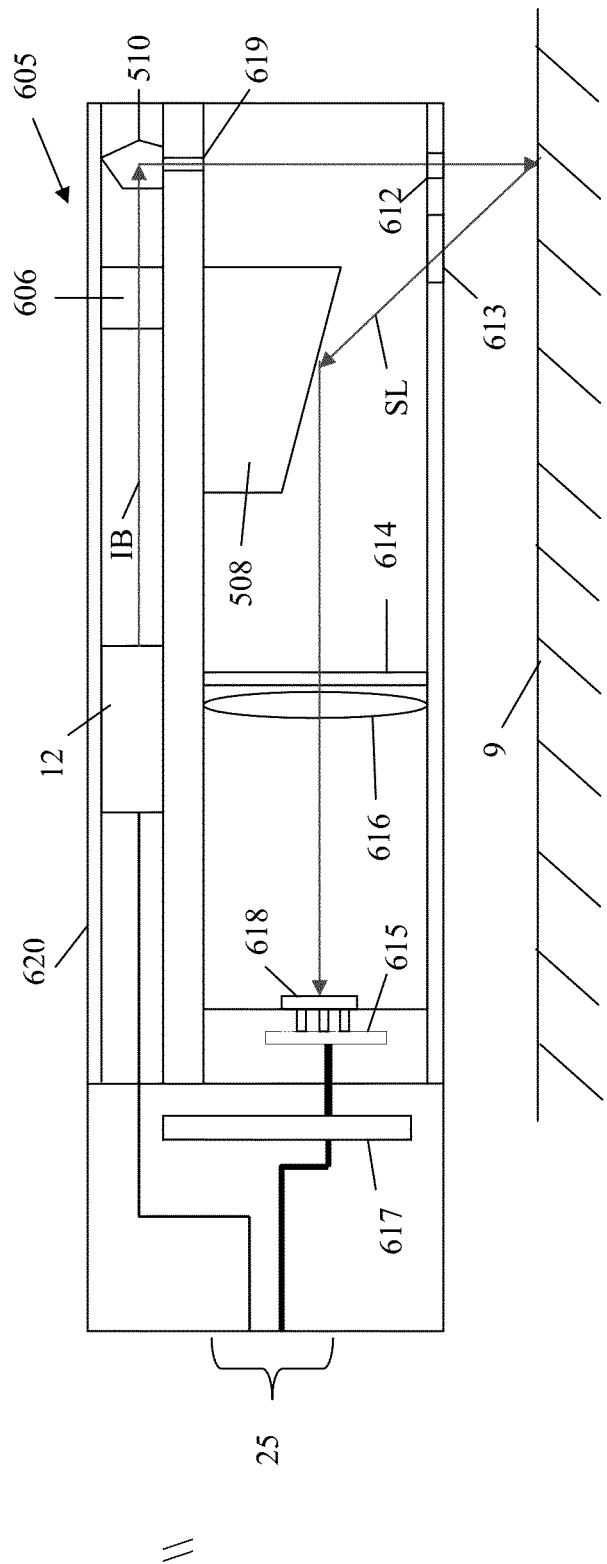
FIG. 6 is a schematic drawing of yet another inspection probe for obtaining imaging and displacement information from the collection of scattered light in accordance with the principles of the present invention.

Probe 505 obtains two dimensional images of the cylinder surface in both reflected and scattered light, but does not determine depth or displacement of the cylinder surface relative to probe 505 at the location that beam IB illuminates surface 9. Probe 605 shown in FIG. 6 can detect displacement with scattered light using triangulation. Probe 605, in addition to components described previously, may include optional beam reducer or focusing optics 606 to reduce the laser spot size on cylinder surface 9, position sensitive detector 618, imaging lens 616, and wavelength filter 614. These components are shielded from the outside environment by probe envelope 620 with opening 612 to permit incident light to reach cylinder surface 9 and opening 613 to permit scattered light to reach mirror 508.

Light beam IB from laser 12 is directed through optional beam reducer or focusing optics 606 into pentaprism 510, which in turn redirects the beam through openings 619 and 612 to surface 9. Scattered light SL from a spot on surface 9 is scattered back through opening 613 to mirror 508 which reflects the scattered beam through wavelength filter 614 and imaging lens 616. Imaging lens 616 projects an image of the spot on cylinder surface 9 onto the surface of detector 618, which senses the position of the imaged spot. This signal indicating the location of the imaged spot on detector 618 can be processed and amplified by preamplifier 615 and electronic circuit 617 and transmitted to data acquisition and processing system 25. Using techniques of triangulation, computer 28 of system 25 can calculate any change in distance between cylinder surface 9 and probe 605 as the probe rotates and scans surface 9. Simultaneously, the total intensity of scattered light collected by detector 618 can be used to produce a two dimensional image of surface 9.

Information about displacement of the scattered light probe in a cylinder enables centering and aligning probe 605 in the cylinder. Such information can also enable determining profile properties of the cylinder such as out-of-round conditions, taper and cylindricity.

A number of different types of detectors can be employed for a position sensing detector. These include, but are not limited to, position sensitive detectors (PSDs) and electronic imaging chips, such as CMOS detectors. A PSD used as detector 618 can quickly determine the centroid of a laser spot on the detector, but a CMOS detector has the advantage that it can produce an image of the laser spot on the detector. The triangulation model can then be used to determine the size of the spot on cylinder surface 9. CMOS detectors, however, have a very large number of pixels that are summed with a weighted average to determine the location of the centroid of the laser spot on the detector.

Figure 7:
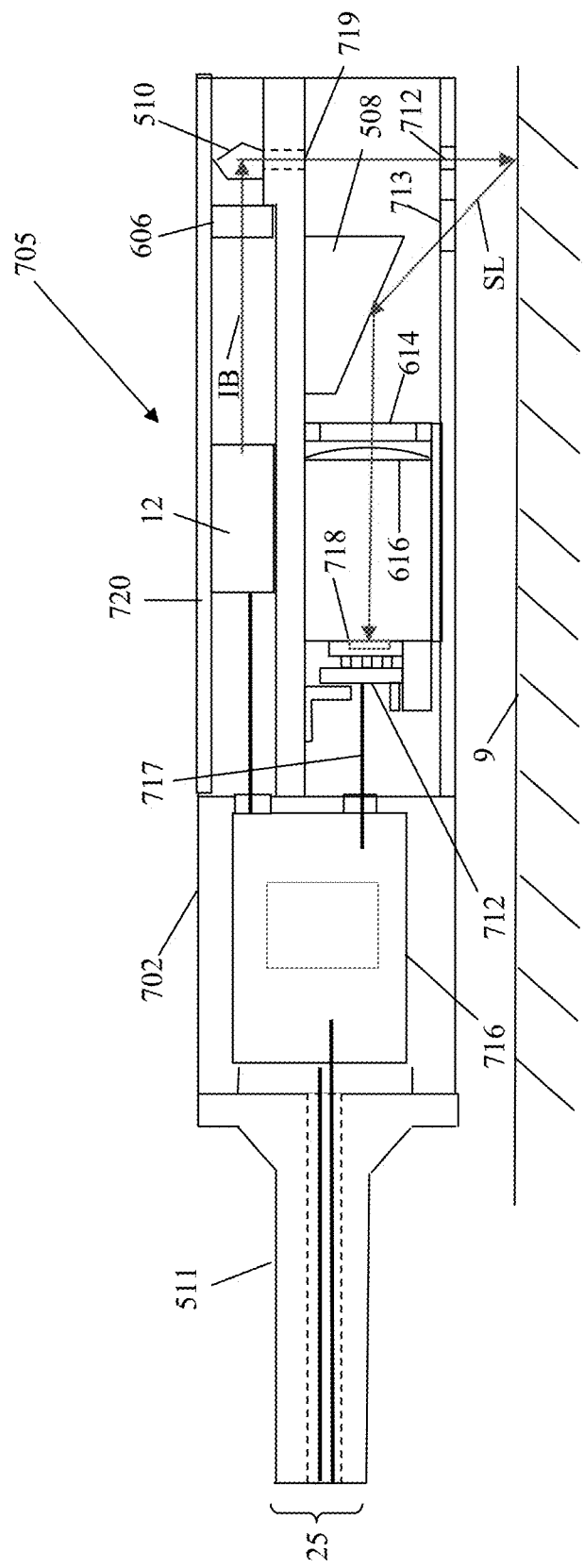
FIG. 7 is a schematic drawing of yet another inspection probe for obtaining imaging and displacement information from the collection of scattered light in accordance with the principles of the present invention.

Probe embodiment 705 of FIG. 7 shows a laser probe employing CMOS detector 718. Calculation of the centroid of the laser spot imaged on detector 718 is performed using electronic processing unit 716 inside probe 705 that transmit the result to data acquisition and processing system 25. These calculations can be programmed in parallel using a small, fast FPGA (Field Programmable Gated Array) board for processing unit 716. Integrated circuit (ASIC) chips could be employed in place of an FPGA as processing unit 716 in probe 705.

In addition, to the components described earlier, probe 705 includes envelope 720 with a pair of openings 712 and 713. Probe housing 702 is connected to probe shaft 511. In this arrangement, laser 12 emits beam IB through optional focusing optics 606 to pentaprism 510, which in turn, directs the beam through opening 719 and openings 712 in probe envelope 720 to cylinder surface 9. Scattered light SL from surface 9 is directed through opening 713 to mirror 508 which reflects scattered light SL through wavelength filter 614 and imaging optics 616 to CMOS detector 718. CMOS detector 718 sends imaging signals to FPGA board 716 through cable 717.

Figure 8:
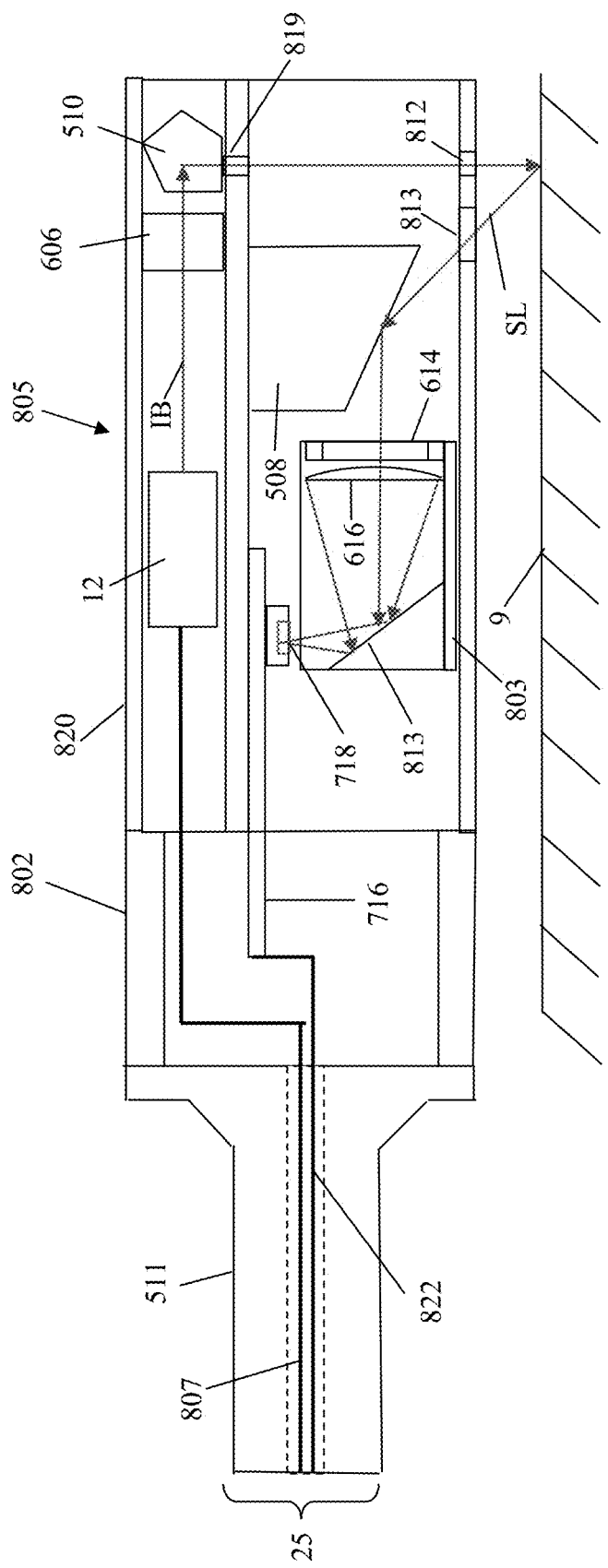
FIG. 8 is a schematic drawing of yet another inspection probe for obtaining imaging and displacement information from the collection of scattered light in accordance with the principles of the present invention.

Another embodiment of a probe incorporating a CMOS detector is probe 805 shown in FIG. 8. Probe 805 includes, in addition to the referenced components described previously, reflecting mirror 813, which could be a right angle prism, that could be mounted within housing 803 together with wavelength filter 614 and imaging optics 616. The probe body 802 is connected to probe shaft 511 through which cables 807 and 822 deliver power to laser 12 and receive signals between probe electronic processing unit 716 and data processing unit 25. In this embodiment CMOS detector 718 is mounted directly onto FPGA board (or ASIC chip) 716 without connecting cable leads.

In probe 805 laser 12 emits beam IB through optional focusing optics 606 to pentaprism 510. Pentaprism 510 directs beam IB through openings 819 and 812 in envelope 820 to surface 9. Scattered light SL is directed through the opening 813 to mirror 508, which directs scattered light SL through optical filter 614 and imaging optics 616. The beam from imaging optics 616 is reflected by mirror 813 to detector 718. The signals from detector 718 are transmitted to electronics board 716, which transmits processed signals to data processing unit 25 through the cable 822.

Accordingly, detector 718 is arranged perpendicular to the probe axis and the laser spot is imaged onto detector 718 with reflector 813, positioned between imaging lens 616 and detector 718.

Windowing of the CMOS chip to reduce the region of interest from which data is transmitted could speed up collection of data from a CMOS detector. This could be done in software. Processing speed could be further increased using a custom designed chip that reduces data collection overhead time by dividing the expected region of interest into independently read parallel rows of pixels.

Figure 9:
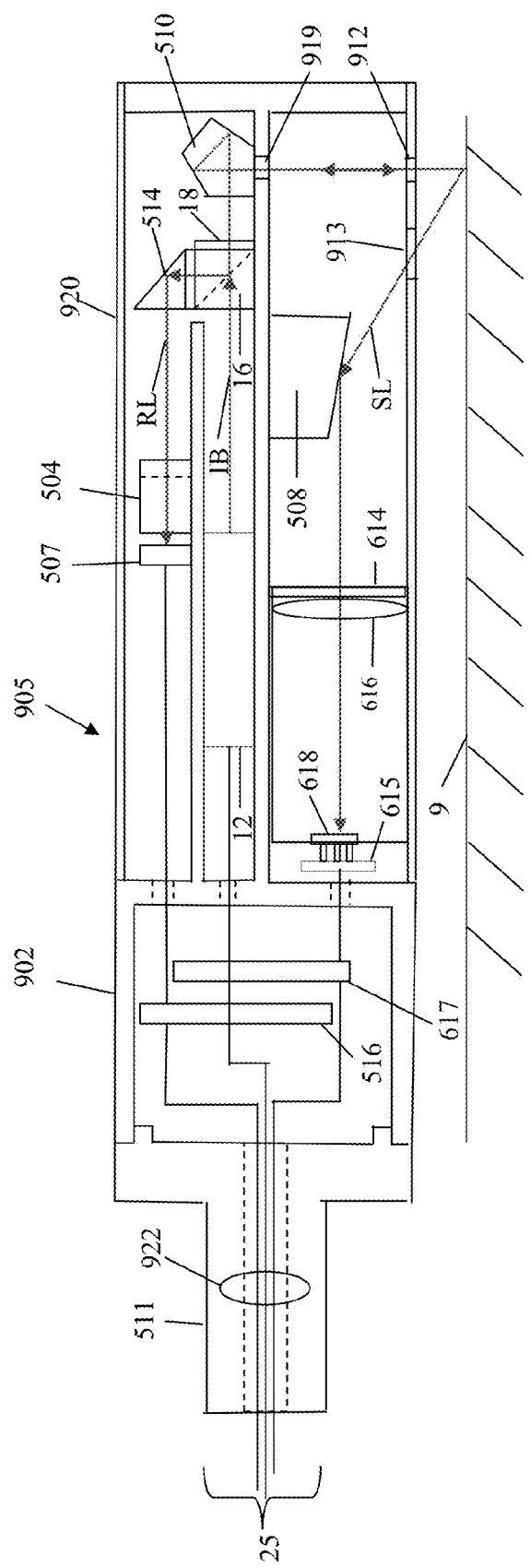
FIG. 9 is a schematic drawing of yet another inspection probe for obtaining both imaging information from reflected light and imaging and displacement information from the collection of scattered light in accordance with the principles of the present invention.

In another arrangement a probe 905 is shown in FIG. 9. Probe 905 is a hybrid probe capable of providing displacement and imaging data from scattered light together with an image of surface 9 using reflected light. Referring to FIG. 9 probe 905 includes position sensitive detector 618 that transmits signals to preamplifier 615 which transmits its processed signals to circuit board 617 in housing 902. Circuit board 617 transmits its processed signals to data acquisition and processing system 25. A second detector 507 transmits its signal to a second electronic circuit board 516 in housing 902 that also transmits its signal to data acquisition and processing system 25. The diameter of this hybrid probe may be greater than a hybrid probe that cannot determine displacement in order to accommodate imaging optics 616.

In probe 905 light beam IB generated by laser 12 is directed through polarizing prism 16 and quarter wave plate 18 toward the pentaprism 510 which redirects light beam IB through opening 919 and opening 912 in probe envelope 920 onto cylinder surface 9. The reflected light RL from surface 9 returns through opening 912 and 919 to pentaprism 510 which redirects reflected light RL to quarter wave plate 18, where its polarization is changed from circular polarization to linear polarization in a direction rotated 90° relative IB. RL is therefore reflected by polarizing beam splitter 16. Reflected light RL is then reflected by right angle prism 514 through the wavelength filter in detector and wavelength filter holder 504 to the detector 507.

Scattered light SL from surface 9 enters probe 905 through opening 913 in envelope 920. Mirror 508 reflects scattered light SL through wavelength filter 614 and imaging optics 616 to PSD 618. Signals from the detectors 507 and 618 are transmitted to the electronic circuit boards 516 and 617 respectively that process the detector signals and transmit them to data acquisition and processing system 25 through cables 922.

Figure 10:
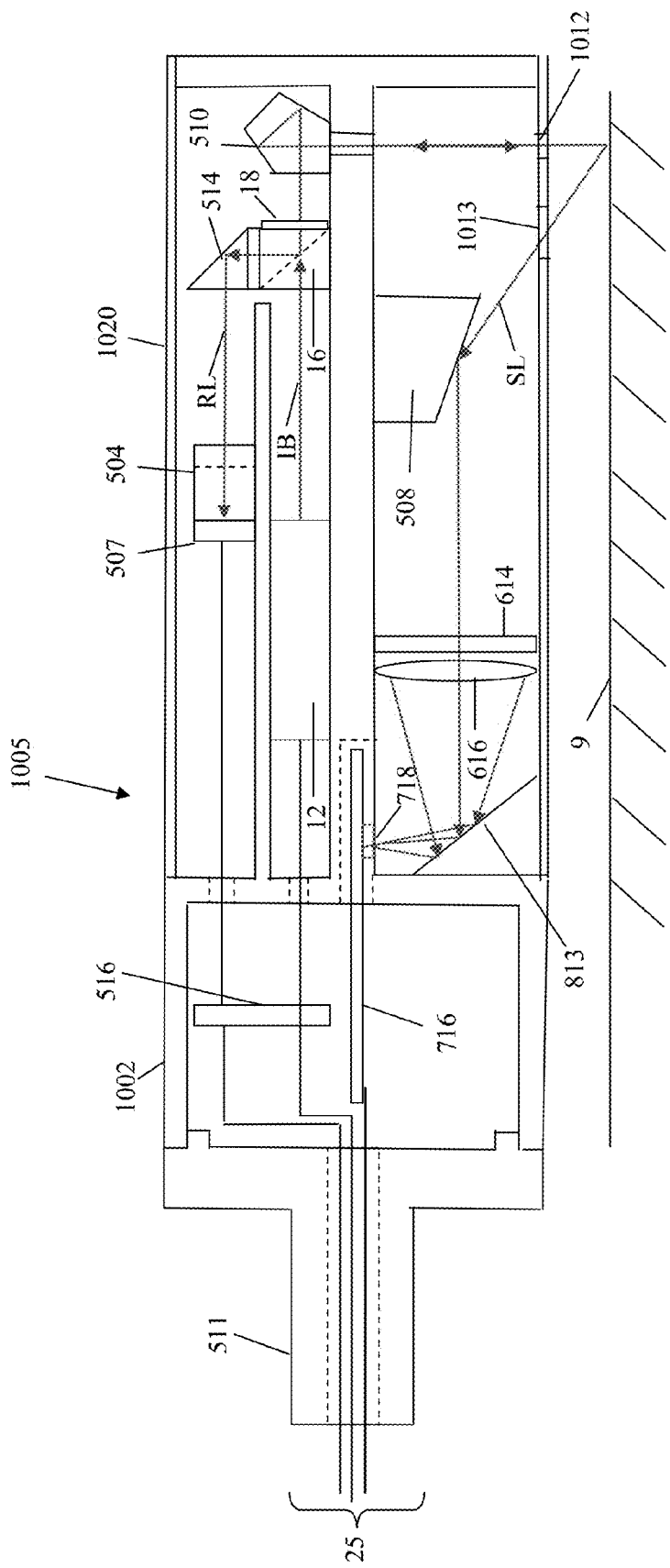
FIG. 10 is a schematic drawing of yet another inspection probe for obtaining both imaging information from reflected light and imaging and displacement information from the collection of scattered light in accordance with the principles of the present invention.

In yet another embodiment a probe 1005 shown in FIG. 10 is a hybrid probe that employs CMOS detector 718 mounted directly on FPGA or ASIC chip 716. Probe 1005 includes certain features of probe 905 combined with certain features of probe 805. Probe 1005 includes various components described earlier along with housing 1002 attached to probe shaft 511. Housing 1002 contains electronic circuit 516 for detector 507 and electronic processing unit 716 for CMOS detector 718.

Figure 11:
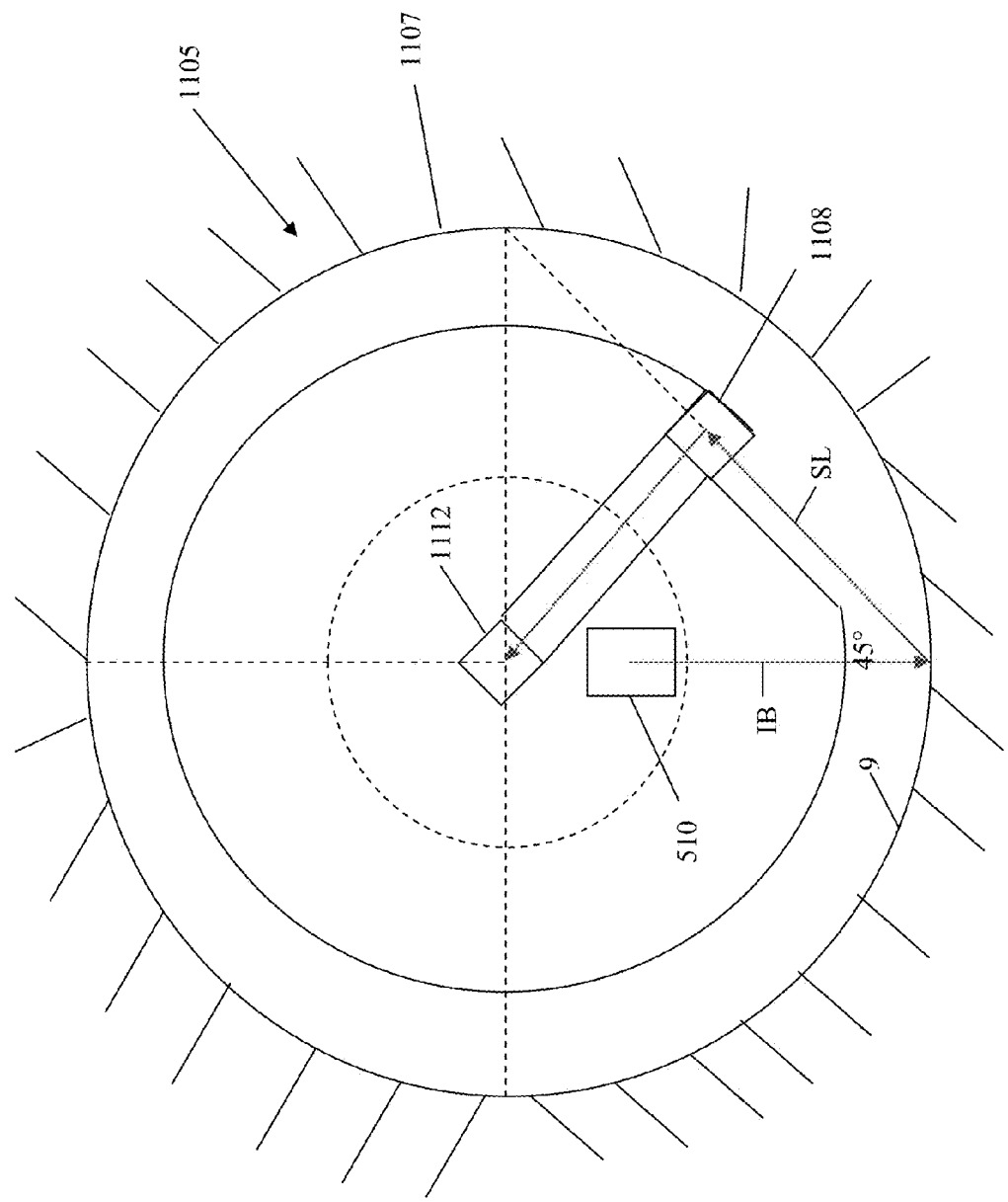
FIG. 11 is a schematic drawing of a component of yet another inspection probe for the collection of scattered light in accordance with the principles of the present invention.

Scattered light detectors may not be able to image the entire surface of a cylinder or accurately measure depth variations in a surface with machined threads or grooves that run perpendicular to the direction in which scattered light is detected by the probe. This may be the case in bored or threaded cylinders and may limit the imaging and displacement capabilities of the scattered light detectors in probes 505 through 1005. One way of addressing this issue is to use optics that collect light in a direction along the grooves and redirect the collected light to a detector aligned to collect light along the probe axis. FIG. 11 shows end cap 1105 that contains this optical configuration.

Laser 12 directs laser beam IB along the axis of a cylindrical probe. Pentaprism 510 redirects laser beam IB onto surface 9 at an angle perpendicular to surface 9. Some of the light scattered in a plane perpendicular to the axis of the cylinder is reflected by right angle mirror or pentaprism 1108 and directed to right angle mirror or pentaprism 1112. Reflector 1112 reflects scattered light SL in a direction parallel to the axis of the probe through a wavelength filter 614 to a scattered light detector. This detector could simply detect the intensity of the light, or, if imaging optics 616 are included in the beam path, could be a detector that detects the location of the image on the detector, such as PSD 618.

Figure 12:
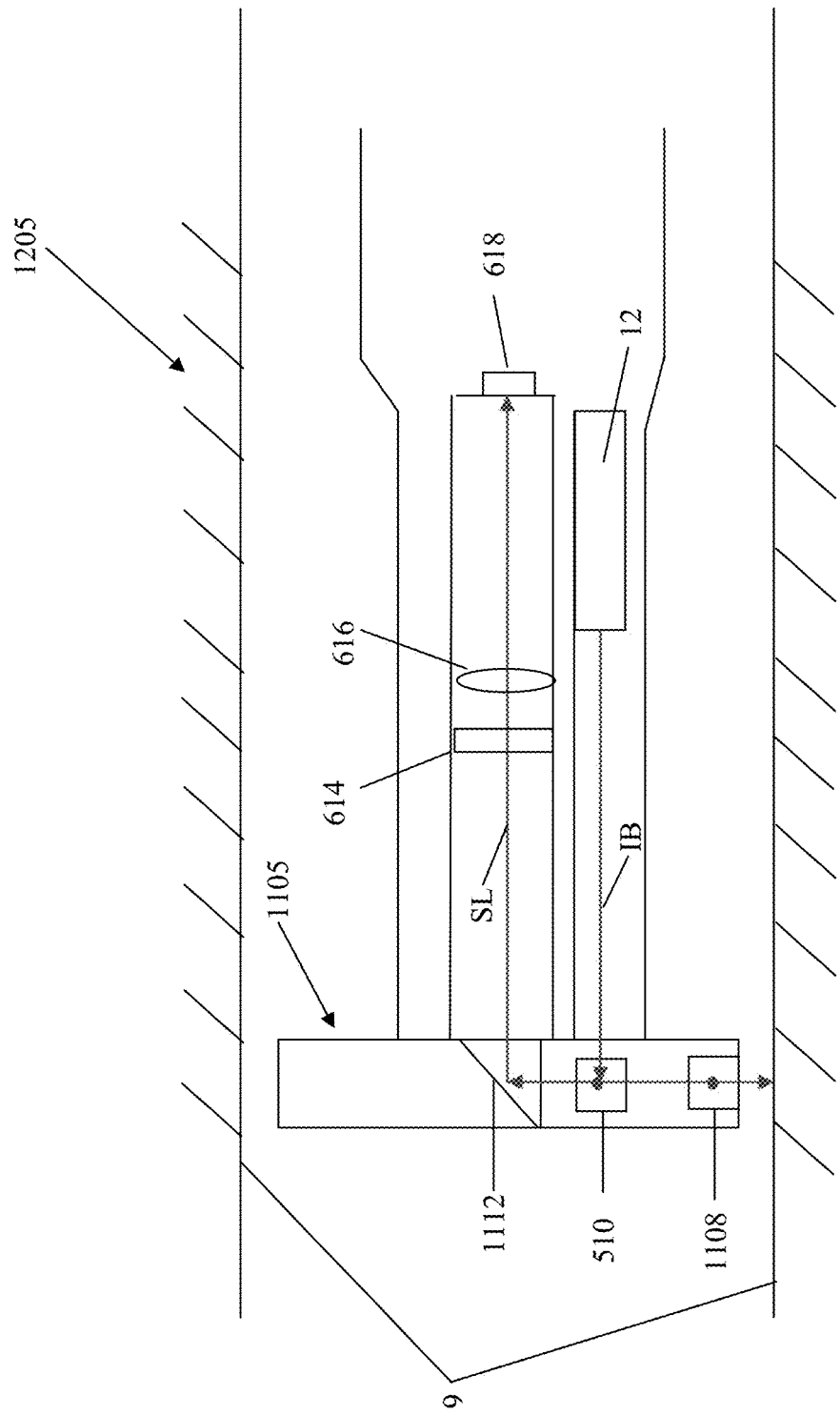
FIG. 12 is a schematic drawing of yet another inspection probe incorporating the component of FIG. 11 in accordance with the principles of the present invention.

End cap 1105 is designed for collecting light from cylinder 1107 of a particular cylinder diameter. Different end caps could be used for different diameter cylinders. FIG. 11 shows a particular end cap design in which light is collected at a 45° angle. End cap 1105 can be used with probe 1205 shown in FIG. 12. Probe 1205 includes a detector 618, a wavelength filter 614 and imaging optics 616.

Laser beam IB from the laser 12 is directed to pentaprism 510 which redirects laser beam IB to cylinder surface 9. Scattered light SL from surface 9 is collected by pentaprism or right angle prism 1108 and reflected to reflector 1112. The center of scattered light beam SL from reflector 1112 passes through the center of probe 1205, through wavelength filter 614 and imaging optics 616 to detector 618. Alternatively, reflector 1112 could be placed at another location along a diameter of probe 1205 and detector 618 could be placed along an axis parallel to the central axis of probe 1205.

Figure 13:
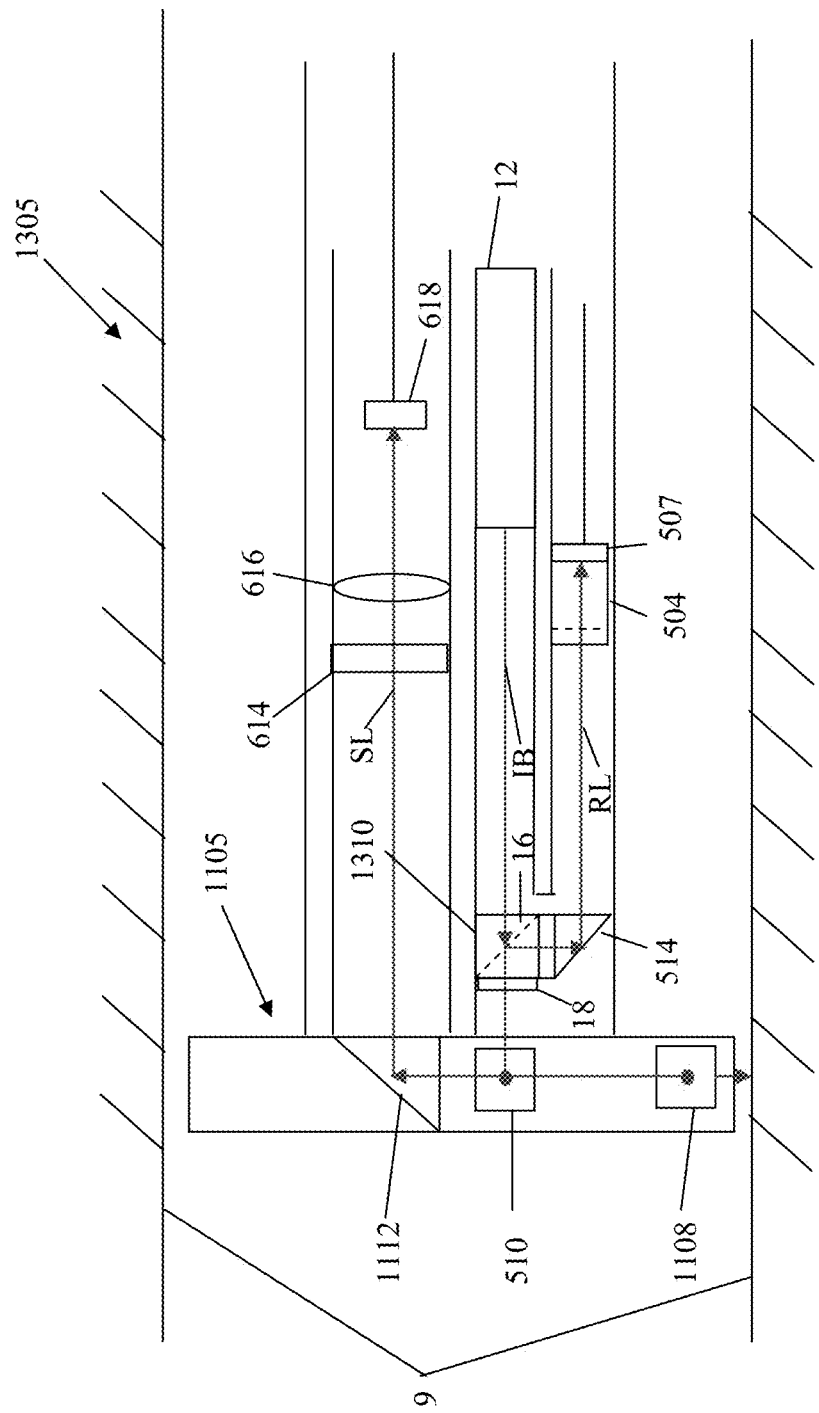
FIG. 13 is a schematic drawing of yet another inspection probe for obtaining both imaging information from reflected light and imaging and displacement information from the collection of scattered light in accordance with the principles of the present invention.

Probe 1305 in FIG. 13 is an embodiment of a hybrid probe that can detect both back reflected light and light scattered in a direction perpendicular to the cylinder axis. In probe 1305 laser 12 emits beam IB that is directed through polarizing prism 16 and quarter wave plate 18 to pentaprism 510 that directs IB to surface 9. Part of the incident beam is directly back reflected through pentaprism 510 to quarter wave plate 18, where it is converted to linear polarization in a direction perpendicular to IB. Reflected light RL is then reflected by polarizing prism 16 and right angle prism 514 through wavelength filter and detector holder 504 to detector 507.

As in detector 1205, some of the scattered light SL emitted in a plane perpendicular to the axis of the cylinder is collected by reflector 1108 and directed to reflector 1112 which redirects scattered light LS through wavelength filter 614 and imaging optics 616 to detector 618.

Figure 14:
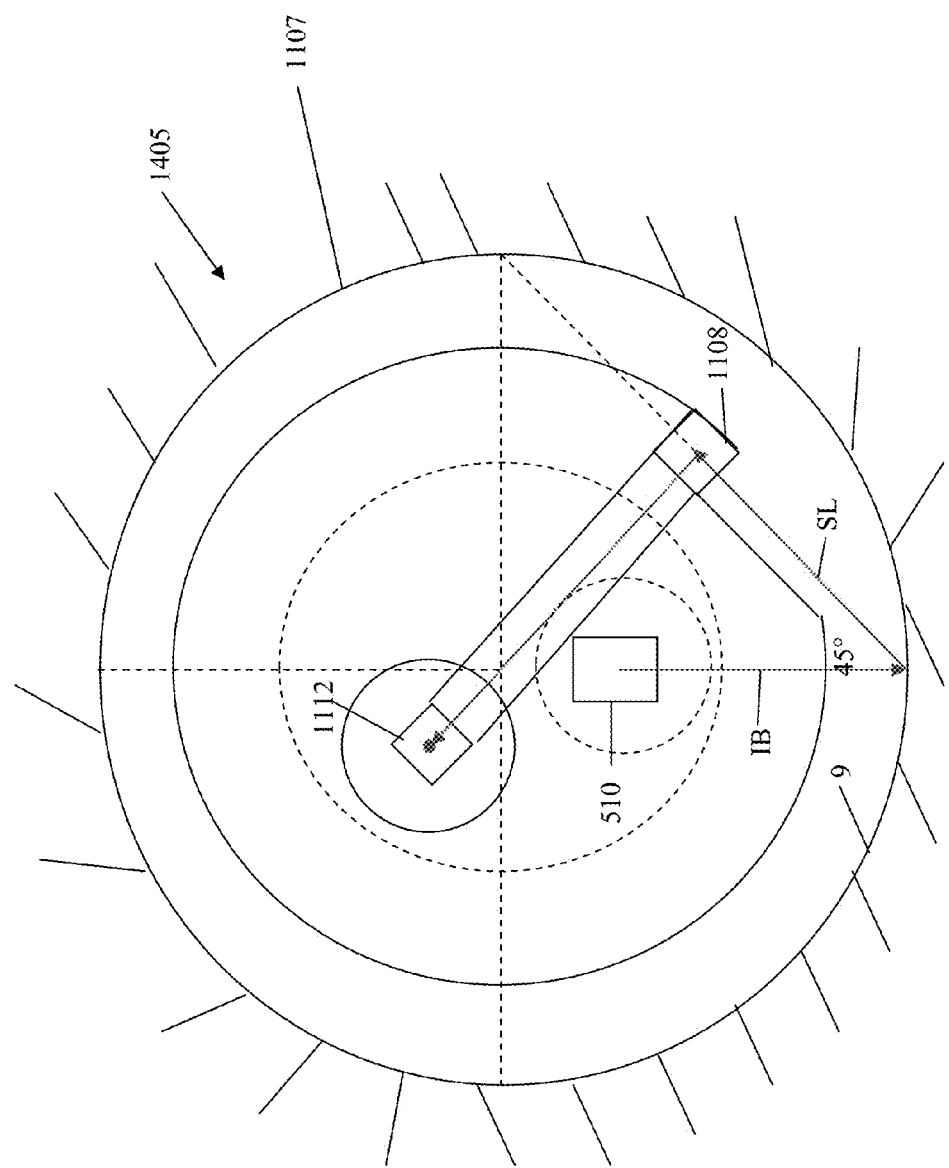
FIG. 14 is a schematic drawing of a component of another inspection probe for the collection of scattered light in accordance with the principles of the present invention.
Figure 15:
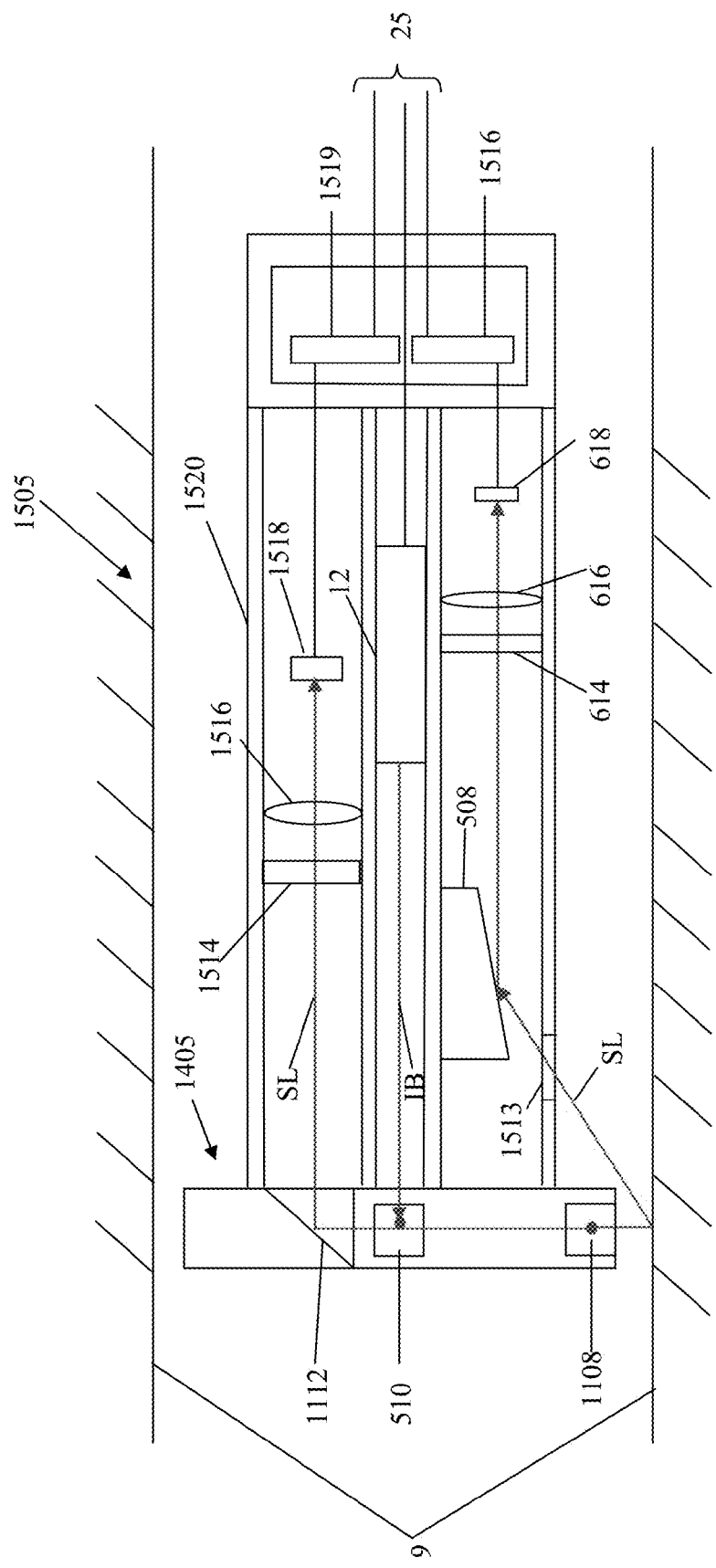
FIG. 15 is a schematic drawing of yet another inspection probe incorporating the component of FIG. 14 in accordance with the principles of the present invention.

Probe 1505 in FIG. 15 shows a probe design that can simultaneously collect scattered light SL scattered along the axis of a cylinder and perpendicular to the axis of a cylinder. Probe 1505 uses end cap 1405 shown in FIG. 14. In probe 1505 laser 12 emits laser beam IB that is deflected by pentaprism 510 to surface 9. Part of beam IB that is scattered in a plane containing the axis of the cylinder, passes through slit 1513 in envelope 1520 of probe 1505 and is reflected by mirror 508 through wavelength filter 614 and imaging optics 616 to detector 618. The signal from detector 618 is processed by electronic circuit 1516 and transmitted to data collection and processing system 25.

Some of incident beam IB that is scattered perpendicular to the axis of the cylinder is collected by reflector 1108 and deflected to reflector 1112 of end cap 1405 where it is deflected through another wavelength filter 1514 and imaging optics 1516 to a second detector 1518. The signal from detector 1518 is processed by electronic circuit board 1519 and transmitted to data collection and processing system 25.

In probes that require power into and data transmission out of a spinning probe, a slip ring or similar mechanical device is employed to transfer power in and signal out of the probe to a data acquisition system and computer that collects and analyzes the data. The slip ring may impose a limit on the rotation speed of the spindle and the number of leads that can be connected to the probe as well as increase the cost and reduce the mean time between failures of the system.

Figure 16:
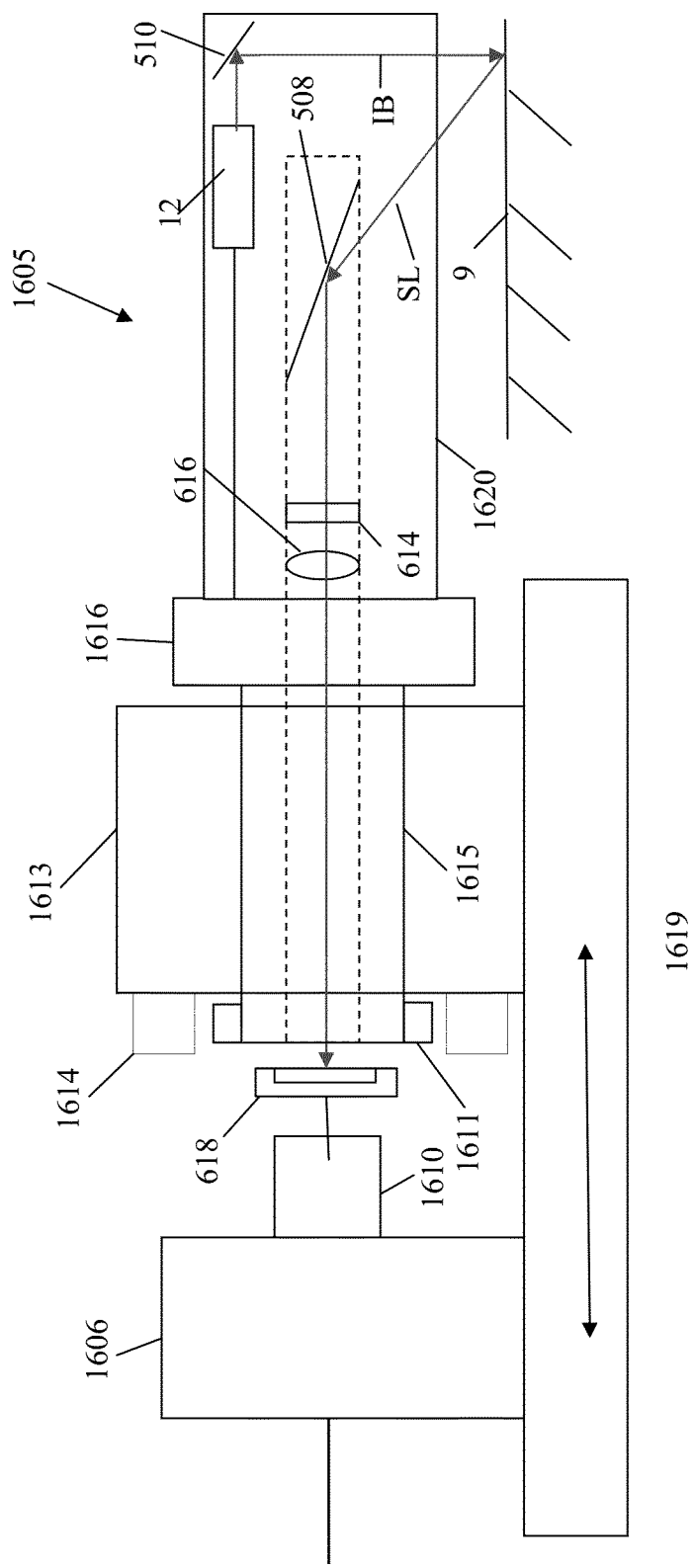
FIG. 16 is a schematic drawing of yet another inspection probe system capable of obtaining imaging and displacement information from the collection of scattered light in accordance with the principles of the present invention.

Probe 1605 in FIG. 16 shows a probe configuration that does not require a slip ring to transmit power into and data out of probe 1605 in which the laser and optics are spinning. Power is transmitted to the laser from a ring lamp 1614 mounted on the stationary body of spindle 1613 concentric with the spindle rotor 1615. Ring lamp 1614 can be an LED ring lamp that is commercially available from camera supply companies. A ring of photodiodes 1611 is mounted on spindle rotor 1615 opposite the ring lamp. Spindle rotor 1615 has a clear through center hole that permits optical signals to be transmitted through it. When ring lamp 1614 is turned on it supplies light to photovoltaic array 1611 that generates an electric current that can be used to power diode laser 12 in probe 1605. It is not necessary that spindle 1613 be spinning in order for ring lamp 1614 to supply power to photovoltaic array 1611. Conditioning electronics may be used to store and process the electrical energy generated by photovoltaic array 1611.

Laser 12 generates a laser beam IB that is directed by pentaprism 510 or other reflector to cylinder surface 9. Scattered light SL passes through a slot in probe envelope 1620 and is reflected by mirror 508 through wavelength filter 614 and imaging optics 616 to detector 618, which is located on the other side of spindle 1613. Detector 618 and the electronics 1610 that process the signal from detector 618 do not rotate, and a slip ring is not required to process this data. Detector 618 and its electronics 1610 are supported by mount 1606 that along with spindle 1613 is mounted on linear motion stage 1619. The probe body is mounted on a tool holder 1616 attached to rotor 1615 of spindle 1613.

A slip ring would also not be needed if the laser probe were used to measure external surfaces of a cylindrical part. In this case the part would spin and the probe could either remain stationary with the part moving linearly or the probe could move along a line to scan the outside surface of a spinning part, such as a gear. Hybrid probes could be used for this application if desired.

This technique for supplying power and obtaining data from a spinning device need not be limited to laser scanning probes. It is applicable to any spinning device requiring electrical power and electrical data connections provided that the data is transmitted optically along the axis of the rotor of a spindle used to spin the tool and is collected outside the tool by a stationary device for collection and processing of optical signals.

Multiple optical signals could be transmitted out of the spinning device through the clear through hole in the spindle rotor provided that the signals are transmitted at different optical wavelengths. Standard optical techniques could then be used to separate the different signals. These could be similar to techniques now used for wavelength division multiplexing.

The aforementioned probes can inspect the interior surface of cylindrical manufactured components in a production environment. When the probe is incorporated into an inspection station that can scan the surface of the cylinder by rotating the laser spot in a helical trajectory along the axis of the cylinder, signals of light, either scattered or directly back reflected from the surface, can be detected by one or more optical detectors that are part of the probe. The probe can also be used to inspect the exterior of cylindrical parts by rotating the part instead of the laser beam.

The probe body design is a particular feature of the probe. If the laser, electronics and optics are contained in a spinning probe body, the probe housing is robust enough to spin at high speed, and a slip ring may be employed to transmit power to the laser and probe electronics and data from the probe to the data collection and analysis system. Alternatively, for detecting reflected light the probe system could be designed so that only the tip of the probe spins in a spindle and the laser and electronics do not spin. This design does not require a slip ring.

The type of defect detection a part manufacturer would need in an inspection system would depend on the intended application for the part being inspected. It is desirable that the inspection system be sufficiently flexible to generate whatever data is needed in a single measurement of the part.

Multiple probes could be operated in parallel to reduce inspection time for a part with multiple cylinders.

The resolution of the probe for detection of defects on the surface of a part is dependent in part on the size of the laser spot on the surface of the part being inspected. The smaller the spot size the better the resolution of the surface that can be achieved. Laser beams generated by single mode fiber lasers can produce small, uniform, round spots because non uniformities in the laser beam are filtered by the cladding of the optical fiber. They may therefore be useful as a laser for scanning surfaces for some embodiments of this invention.

In the process of filtering the beam in an optical fiber, beam polarization is scrambled, so that an initially linearly polarized beam input to a fiber laser will have polarization components in two orthogonal directions at the output end of the fiber. This could be a problem when beam polarization is used to separate the laser beam incident on a cylindrical surface from the return beam to the detector. There are polarization preserving fibers, but these produce larger elliptical output beams that cannot be focused to as small a spot as a single mode fiber.

What is claimed is:

1. A non-contact optical probe for inspecting a surface of a cylindrical workpiece comprising:
   a laser source that emits an incident light beam;
   a first reflector that directs the incident light beam onto the surface;
   a second reflector that receives scattered light from the surface;
   an optical system that images the spot of scattered light on the cylinder surface onto the surface of a detector, the detector receiving the scattered light from the imaging system and generating signals that provide imaging data and displacement information through triangulation.

2. The non-contact probe of claim 1 wherein the surface is the inside surface of a cylinder.

3. The non-contact probe of claim 1 further comprising a wavelength filter positioned between the second reflector and the detector.

4. The non-contact probe of claim 1 wherein the detector is a position sensitive detector.

5. The non-contact probe of claim 1 wherein the detector is a CMOS detector.

6. The non-contact probe of claim 5 wherein the detector communicates with a field programmable gated array or application specific integrated circuit that processes signals from the detector.

7. The non-contact probe of claim 1 further comprising an end cap containing the first reflector that directs the incident beam perpendicular to a cylinder surface, the end cap collecting light scattered in a plane perpendicular to the axis of the cylinder.

8. The non contact probe of claim 1 wherein power to the laser is generated by a ring of photovoltaic detectors mounted on a rotor of a spindle rotating the probe, the photovoltaic array receiving its power from a ring lamp concentric with the array.

9. The probe of claim 8 wherein the spindle rotor has a clear through hole through which the optical signal is transmitted to a non-rotating detector centered on the spindle axis.

* * * * *